(12) United States Patent
Sugisawa

(10) Patent No.: US 8,221,312 B2
(45) Date of Patent: Jul. 17, 2012

(54) ENDOSCOPE

(75) Inventor: Tatsuya Sugisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 682 days.

(21) Appl. No.: 12/362,211

(22) Filed: Jan. 29, 2009

(65) Prior Publication Data

US 2009/0198105 A1    Aug. 6, 2009

(30) Foreign Application Priority Data

Feb. 1, 2008 (JP) ................................. 2008-022508
Sep. 25, 2008 (JP) ................................. 2008-245245

(51) Int. Cl.
*A61B 1/04* (2006.01)
*A61B 1/12* (2006.01)

(52) U.S. Cl. ......... 600/153; 600/130; 600/156; 600/158
(58) Field of Classification Search ................. 600/104, 600/128, 130, 153, 156, 158, 182, 159
See application file for complete search history.

(56) References Cited

U.S. PATENT DOCUMENTS

| | | | | |
|---|---|---|---|---|
| 3,924,608 A | * | 12/1975 | Mitsui | 600/159 |
| 5,738,630 A | * | 4/1998 | Suzuki et al. | 600/121 |
| 2002/0040181 A1 | * | 4/2002 | Arai et al. | 600/156 |
| 2005/0107662 A1 | * | 5/2005 | Smith | 600/104 |
| 2005/0203341 A1 | * | 9/2005 | Welker et al. | 600/130 |
| 2007/0066869 A1 | * | 3/2007 | Hoffman | 600/153 |

FOREIGN PATENT DOCUMENTS

| JP | 2001-128937 A | 5/2001 |
|---|---|---|
| JP | 3590199 B2 | 8/2004 |

* cited by examiner

*Primary Examiner* — Matthew J Kasztejna
*Assistant Examiner* — Kevin G Barry, III
(74) *Attorney, Agent, or Firm* — Sughrue Mion, PLLC

(57) ABSTRACT

An air/water channel is split into smaller-diameter branch channels before the air/water channel enters a bending portion so as to create a space within a joint ring constituting the bending portion. A forceps channel having the largest outer diameter among internal components of the joint rings is disposed at the center of the joint rings. In addition to the branch channels, optical fibers as a light guide, a signal line, and the like are arranged around the forceps channel within the joint rings. By eliminating the created space, a diameter of the joint rings is reduced and thus a diameter of an insertion section is reduced.

11 Claims, 9 Drawing Sheets

ENDOSCOPE

FIELD OF THE INVENTION

The present invention relates to an endoscope for performing a biopsy of affected tissue, or the like, while images in a body cavity are observed.

BACKGROUND OF THE INVENTION

A medical diagnosis using an endoscope has been common in the medical field. The endoscope has an insertion section and an operating section. The insertion section is inserted in a body cavity. The operating section is provided at a base end of the insertion section. A distal tip of the insertion section is a rigid portion incorporating an image taking device having an imaging element such as a CCD. Image signals taken by the CCD are subject to signal processing in a processor. Thereby, images in the body cavity are observed on a monitor or the like. The insertion section is provided with a forceps channel through which a medical instrument (treatment instrument) is inserted into the body cavity. Such medical instrument is used for performing a biopsy of affected tissue, or the like, while images of the inside of the body cavity are observed.

At a base end of the rigid portion is provided a bending portion in which plural (for example, 16) joint rings are connected in series. Each joint ring has a cylindrical body, a pair of outer projections, and a pair of inner projections. The outer projections extend out from one side of the cylindrical body in an axis direction of the insertion section. The inner projections extend out from the other side of the cylindrical body in the axis direction. The outer projection and the inner projection are shifted from each other by 90° in a circumferential direction of the cylindrical body. A coupling hole is formed to penetrate each of the inner and outer projections. The outer projection and the inner projection of the adjacent joint rings are overlapped and coupled rotatably with a coupling pin which is inserted through the coupling holes. Two pairs of operation wires are provided along in the joint rings for moving the joint rings in an up-and-down direction and a right-and-left direction. Pushing or pulling the operation wires rotates the joint rings and bends the bending portion.

The operating section is provided with an angle knob for pushing or pulling the operation wires. The bending portion is bent in the up-and-down direction or the right-and-left direction by operating the angle knob. Thus, the rigid portion is directed to a desired direction.

Various attempts have been made to reduce a diameter of the insertion section of the conventional endoscope configured as above. For example, in Japanese Patent Laid-Open Publication No. 2001-128937, a signal cable in which signal lines extending from an imaging device are bound together is split into plural signal cables. Of those, the signal cable having the largest diameter is disposed within or close to a space having the largest diameter between an outer perimeter of a forceps channel and an inner circumferential surface of an insertion section. The forceps channel has the largest outer diameter among internal components arranged within the insertion section. The outer diameters of the signal cable having the largest diameter and the rest of the signal cables are set so as to make an inner diameter of the space, in which the signal cables are arranged, a minimum.

In Japanese Patent No. 3590199, operation wires for bending a bending portion are branched. Such branched operation wires are arranged so as not to come in contact with other internal components.

Such attempts reduced the diameter of the insertion section, which replaced the conventional oral endoscope adapted to be inserted through a mouth with a nasal endoscope adapted to be inserted through a nostril. The diameter of the insertion section of the nasal endoscope is at most 6 mm.

The joint rings are necessary for the bending portion regardless of whether it is an oral endoscope or a nasal endoscope. A diameter of the insertion section is determined based on a diameter of the bending portion. For example, as shown in FIG. 9, coupling pins 103 for coupling adjacent joint rings 101 are disposed in a bending portion 102 constituted with joint rings 101. For this reason, it is necessary to arrange internal components in the joint rings 101 such that the internal components don't come in contact with the coupling pins 103. Therefore, an arrangement of the internal components in the bending portion 102 is a key factor for reducing the diameter of the insertion section. The bending portion 102 has a configuration in which a forceps channel 104, optical fibers 105 as a light guide, an air/water channel 106, a signal line 107, and the like are arranged. The forceps channel 104 has the largest diameter among the above-mentioned internal components in the bending portion 102, and is disposed at the center of the joint rings 101 in the diameter direction. The optical fibers 105, the air/water channel 106, the signal line 107, and the like are disposed around the forceps channel 104 and contact with inner circumferential surfaces of the joint rings 101 while they are kept away from the coupling pins 103. An operation wire 109 used for bending the bending portion 102 is threaded through a guide hole 108 formed in the coupling pin 103.

As shown in FIG. 9, diameters of the optical fibers 105 and the signal line 107 are reduced by virtue of the selection of materials. On the other hand, the diameter of the air/water channel 106 is still large relative to the optical fibers 105 and the signal line 107. Therefore, improvements in the arrangement of the air/water channel 106 would further reduce the diameter of the insertion section. Although Japanese Patent Laid-Open Publication No. 2001-128937 and Japanese Patent No. 3590199 disclose to reduce the diameter of the insertion section by splitting the signal line or the operation wire, there are no improvements on the air/water channel and no significant solutions to reduce the diameter of the air/water channel. In addition, in the method disclosed in Japanese Patent No. 3590199, the operation wire may break due to stress concentration at a branch point of the operation wire, resulting in medical accidents.

SUMMARY OF THE INVENTION

An object of the present invention is to provide an endoscope having an insertion section with a further reduced diameter.

In order to achieve the above objects and other objects, an endoscope of the present invention includes a forceps channel for inserting a medical instrument into a body cavity, an air/water channel for feeding at least one of air and water, and an insertion section through which the forceps channel and the air/water channel are disposed. The insertion section has a bending portion close to a distal tip of the insertion section. The air/water channel is split into plural branch channels (for example, two branch channels) before entering the bending portion, and the branch channels pass through the bending portion.

It is preferable that an outer area of a cross-section of each of the branch channels is smaller than an outer area of a cross-section of the air/water channel. The cross-section of each of the branch channels is vertical to an axis direction of each of the branch channels. The cross-section of the air/water channel is vertical to an axis direction of the air/water channel.

It is preferable that the branch channels are merged after passing through the bending portion.

It is preferable that the branch channels are arranged along a circumferential direction of the bending portion.

It is preferable that an outer shape of the branch channel is circular in cross-section vertical to the axis direction of the branch channel.

It is preferable that an outer shape of the branch channel is ellipsoidal or flat-shaped in cross-section vertical to the axis direction. In this case, it is preferable that an inner shape of the branch channel is circular in cross-section vertical to the axis direction.

It is preferable that a signal line for transmitting an image signal and a light guide for guiding illumination light are disposed through the insertion section. It is preferable that each of the signal line and the light guide is covered with a tube, and an outer shape of at least one of the signal line and the light guide is ellipsoidal or flat-shaped in cross-section vertical to an axis direction of the signal line or the light guide at least within the bending portion.

It is preferable that an inner shape of the tube covering the signal line is circular in cross-section vertical to the axis direction of said signal line, and an inner shape of the tube covering the light guide is circular in cross-section vertical to the axis direction of said light guide.

It is preferable that the endoscope is a nasal endoscope whose insertion section is inserted through a nostril.

According to the endoscope of the present invention, the air/water channel is split into two or more branch channels in the bending portion. As a result, a diameter of each of the branch channels is reduced. Thereby, the diameter of the insertion section is reduced.

Since the outer shape of the branch channel is ellipsoidal or the flat-shaped in cross-section vertical to the axis direction, bending stiffness (bending strength) of the branch channel within the bending portion is increased compared to a case where the outer shape of the branch channel is circular in cross-sections. As a result, the air/water channel is prevented from damages such as buckling caused by bending operation of the bending portion.

In a case where at least one of the outer shapes of the signal line and the light guide are ellipsoidal in cross-sections vertical to the axis directions of the signal line and the light guide, respectively, at least within the bending portion, bending stiffness of the signal line and the light guide is increased compared to a case where the outer shapes of the signal line and the light guide are circular in cross-sections. As a result, the signal line and the light guide are prevented from damages such as buckling caused by bending operation of the bending portion.

BRIEF DESCRIPTION OF THE DRAWINGS

The above objects and advantages of the present invention will become more apparent from the following detailed description when read in connection with the accompanying drawings, in which.

DESCRIPTION OF THE PREFERRED EMBODIMENTS

First Embodiment

Figure 1:
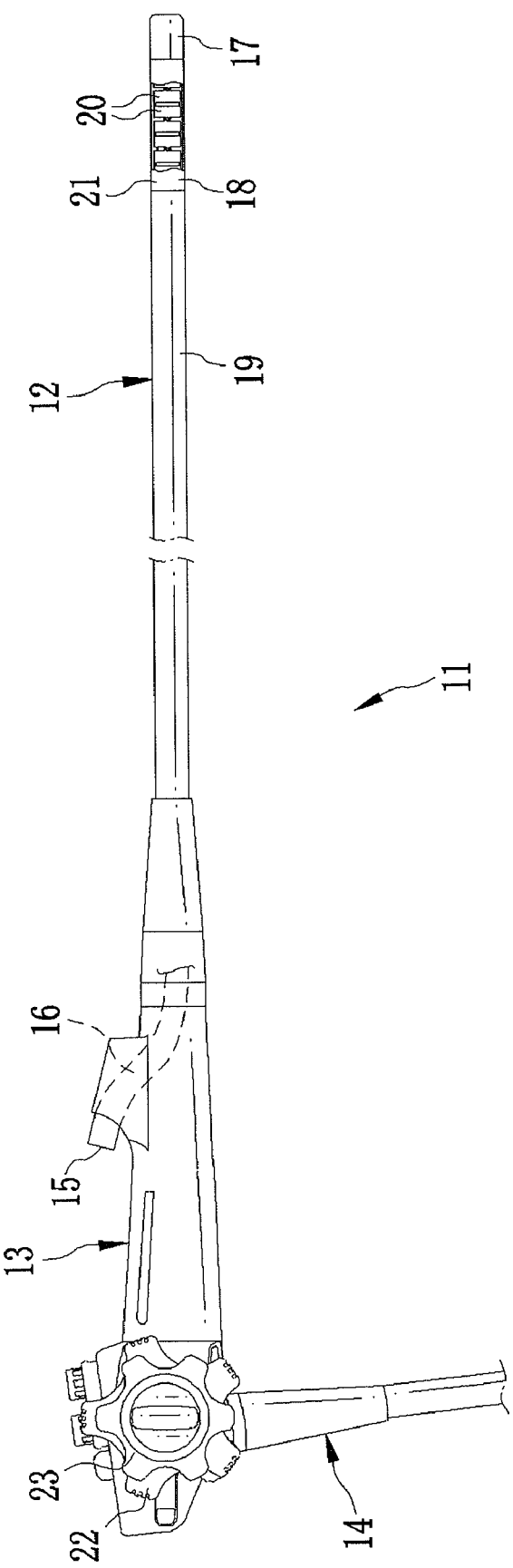
FIG. 1 is an external view of an endoscope.

As shown in FIG. 1, an electronic endoscope (hereinafter referred to as endoscope) 11 is provided with an insertion section 12, an operating section 13, and a universal cord 14. The insertion section 12 is inserted in a body cavity. The operating section 13 is connected to a base end portion of the insertion section 12. The universal cord 14 is connected to the operating section 13. The operating section 13 is provided with a forceps inlet 15 through which a medical instrument (treatment instrument) is inserted. As shown by dashed lines in FIG. 1, the forceps inlet 15 is connected to a forceps channel 16 disposed through the insertion section 12.

The insertion section 12 has a rigid portion 17, a bending portion 18, and a flexible portion 19. The rigid portion 17 is provided at a distal tip of the insertion section 12. The bending portion 18 is connected to a base end of the rigid portion 17. The flexible portion 19 is connected to a base end of the bending portion 18.

The rigid portion 17 incorporates an objective lens and an imaging unit having an imaging element (all not shown). Image light reflected from an object of interest in the body cavity is captured by the imaging element through the objective lens. Image signals obtained by the imaging element are sent to a processor (not shown) connected to the universal cord 14 through a signal line 51 (see FIG. 4) provided through the insertion section 12 and the operating section 13. In the processor, the image signals are subject to predetermined image processing and then displayed as an endoscopic image on a monitor (not shown).

The rigid portion 17 is provided with a light window (not shown). Illumination light from a light source device (not shown) connected to the universal cord 14 is guided to the light window using optical fibers 50 (see FIG. 4) provided as a light guide to extend through the insertion section 12 and the operating section 13. The illumination light is emitted from the light window to the object of interest. The rigid portion 17 is provided with a forceps outlet and a nozzle (both not shown). The forceps outlet is connected to the forceps channel 16 provided through the insertion section 12. The nozzle is connected to an air/water channel 41 (see FIG. 4) provided through the insertion section 12.

The bending portion 18 is constituted of plural (for example, 16) joint rings 20 connected in series, and bendable rubber (angle rubber) 21 covering an outer periphery of the joint rings 20. The joint ring 20 located next to the rigid portion 17 is fixed to the rigid portion 17. The bending portion 18 bends up or down in accordance with operation of an up-and-down angle knob 22. The bending portion 18 bends right or left in accordance with operation of a right-and-left angle knob 23. The up-and-down angle knob 22 and the right-and-left angle knob 23 are provided in the operating section 13. The rigid portion 17 is directed toward a desirable direction in the body cavity by bending the bending portion 18 with operation of the up-and-down and the right-and-left angle knobs 22 and 23. The flexible portion 19 is several meters long to make the rigid portion 17 reach an intended site in the body cavity.

Figure 2:
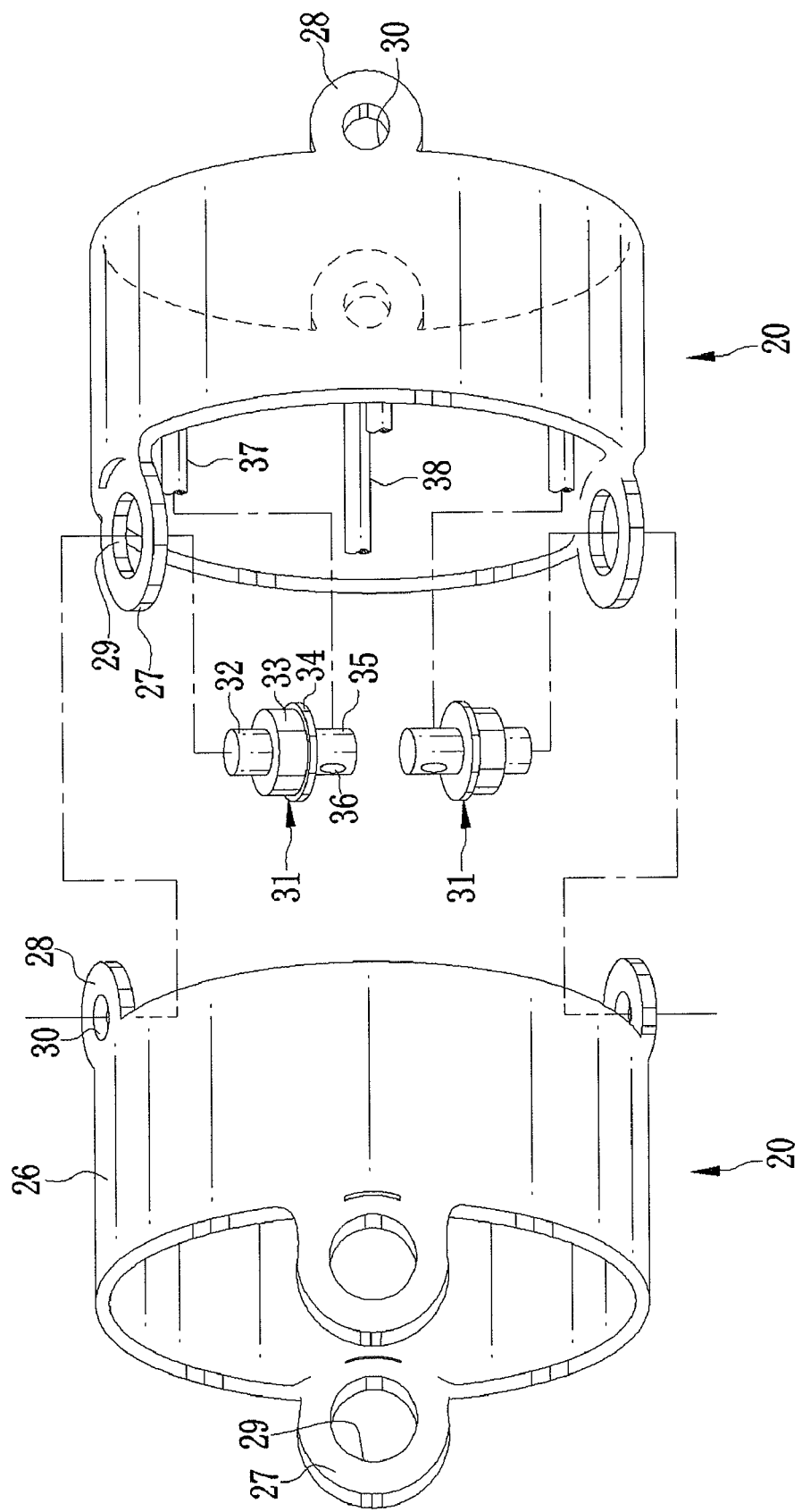
FIG. 2 is an exploded perspective view of a mechanism for connecting joint rings.

As shown in FIG. 2, each joint ring 20 has a cylindrical body 26, a pair of inner projections 27, and a pair of outer projections 28. The inner projections 27 extend out from one end of the cylindrical body 26 to the rigid portion 17 side, and face each other. The outer projections 28 extend out from the other end on the cylindrical body 26 to the flexible portion 19 side, and face each other.

The inner projections 27 are substantially disc-shaped. A coupling hole 29 is formed through a center of each inner projection 27. The outer projections 28 are substantially disc-shaped smaller than the inner projections 27. A coupling hole 30 smaller than the coupling hole 29 is formed through a center of each outer projection 28. The pair of the inner projections 27 and the pair of the outer projections 28 are shifted from each other by 90° in the circumferential direction of the cylindrical body 26. The inner projection 27 is positioned inward, in the diameter direction of the cylindrical body 26, from the outer projection 28 by an approximate plate thickness of the cylindrical body 26.

The adjacent joint rings 20 are coupled using coupling pins 31. Each coupling pin 31 has a small diameter section 32, a large diameter section 33, an end stop section 34, and a wire guide section 35, and these sections have cylindrical shapes. Adjacent joint rings 20 are circumferentially displaced by 90° from each other, and the inner projection 27 and the outer projection 28 of the adjacent joint rings 20 are overlapped. The large diameter section 33 is put in the coupling hole 29 of the inner projection 27, and the small diameter section 32 is put in the coupling hole 30 of the outer-projection 28. The inner surface of the outer projection 28 comes in contact with an end of the large diameter section 33. Thus, the joint rings 20 are rotatably coupled. Then, an end of the small diameter section 32 is crimped so as to prevent the coupling pin 31 from falling off from the joint rings 20. In particular, the thickness of the large diameter section 33 in an axis direction of the coupling pin 31 is larger than the plate thickness of the inner projection 27. Thereby, a clearance is created between the inner projection 27 and the outer projection 28, and between the inner projection 27 and the end stop section 34. Thus, the joint rings 20 rotate smoothly.

A guide hole 36 is formed through the wire guide section 35 in the diameter direction of the wire guide section 35. An up-and-down operation wire 37 or a right-and-left operation wire 38 (hereinafter may simply be referred to as operation wires 37, 38) is threaded through the guide hole 36. An end of each of the operation wires 37 and 38 is fixed to the rigid portion 17. The other end thereof is passed through the bending portion 18, the flexible portion 19, and the operating section 13. The other end thereof is hooked around a pulley (not shown) and turned over in the operating section 13, and fixed to the rigid portion 17. The pulley is rotated in accordance with the operation of the up-and-down angle knob 22 and the right-and-left angle knob 23 (both see FIG. 1). When the up-and-down angle knob 22 is operated, the up-and-down operation wires 37 are pushed and pulled. When the right-and-left angle knob 23 is operated, the right-and-left operation wires 38 are pushed and pulled.

Figure 3:
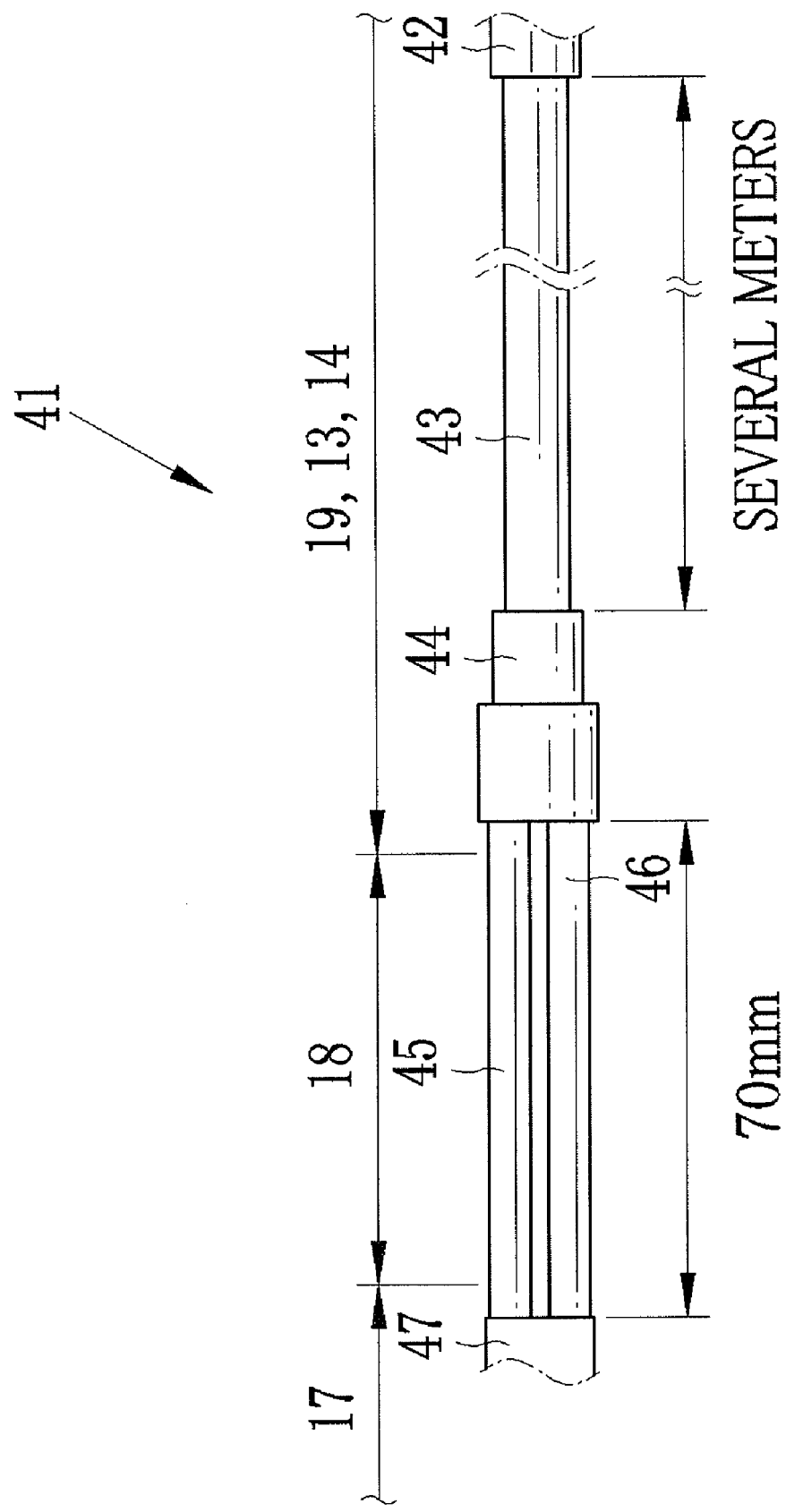
FIG. 3 is a schematic view of an air/water channel.

The endoscope 11 incorporates the air/water channel 41 as shown in FIG. 3. The air/water channel 41 has a base end section 42, a splitting section 44, a main channel 43, two branch channels 45 and 46, and a merging section 47. The base end section 42 is connected to an air/water supply pump (not shown). The main channel 43 is connected to the base end section 42. The splitting section 44 is connected to a front end of the main channel 43 in a flow direction and splits the flow of the main channel 43 into two branch channels 45 and 46. One end of the merging section 47 is connected to the front ends of the two branch channels 45 and 46 in the flow direction to merge the flows of the branch channels 45 and 46 into one, and the other end thereof is connected to a nozzle (not shown) provided in the rigid portion 17.

The main channel 43 is several meters long. The length of the main channel 43 is approximately equal to a total length of the flexible portion 19, the operating section 13, and the universal cord 14. Each of the branch channels 45 and 46 is, for example, 70 mm long, although depending on the length of the bending portion 18. Each of the branch channels 45 and 46 is made a little longer than the bending portion 18 so that the branch channels 45 and 46 can extend throughout the bending portion 18. An outer diameter of each of the branch channels 45 and 46 is smaller than that of the main channel 43 (for example, the outer diameter of each of the branch channels 45 and 46 is 0.7 times as large as that of the main channel 43).

Figure 4:
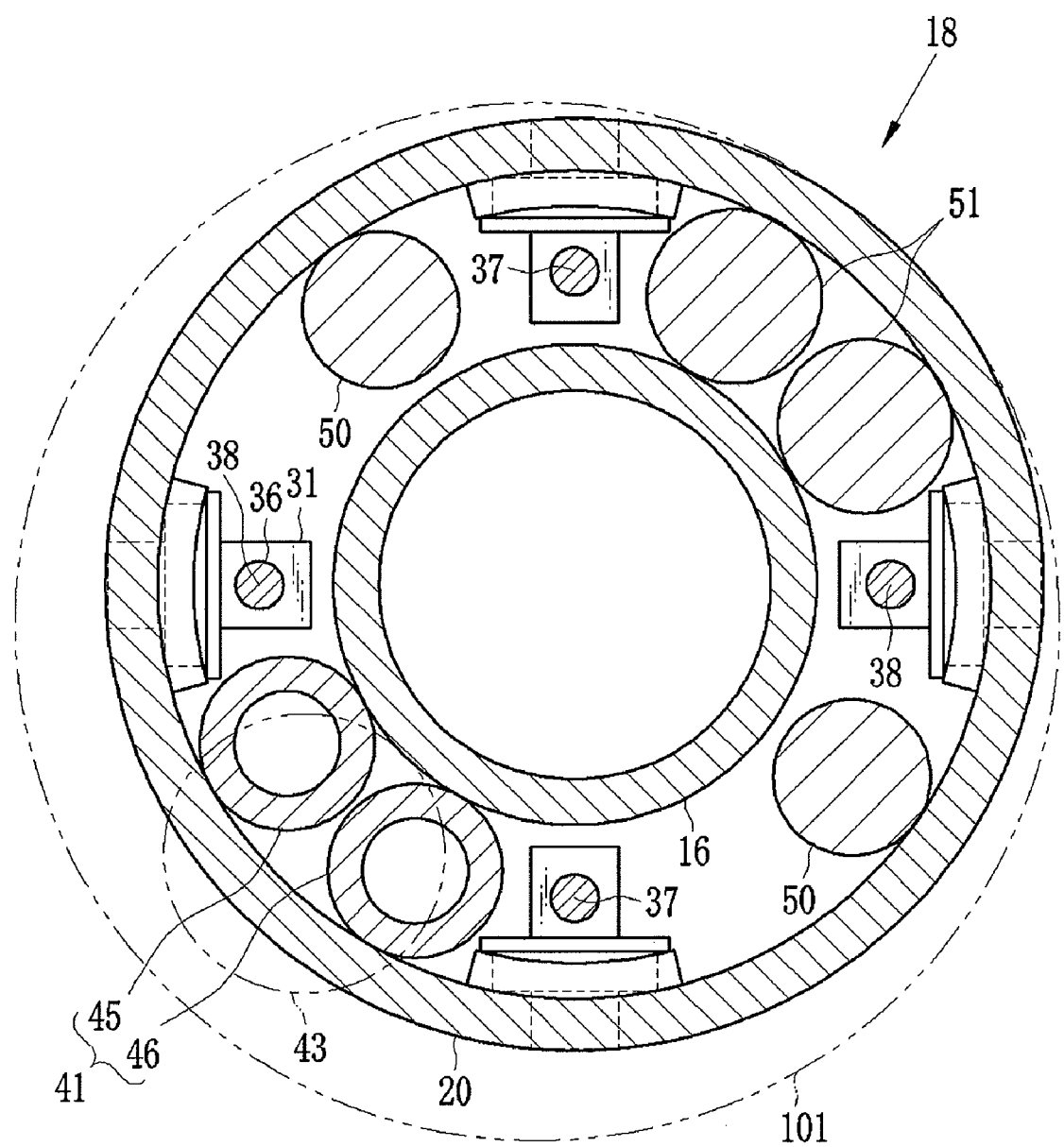
FIG. 4 is a section view of a bending portion.
Figure 9:
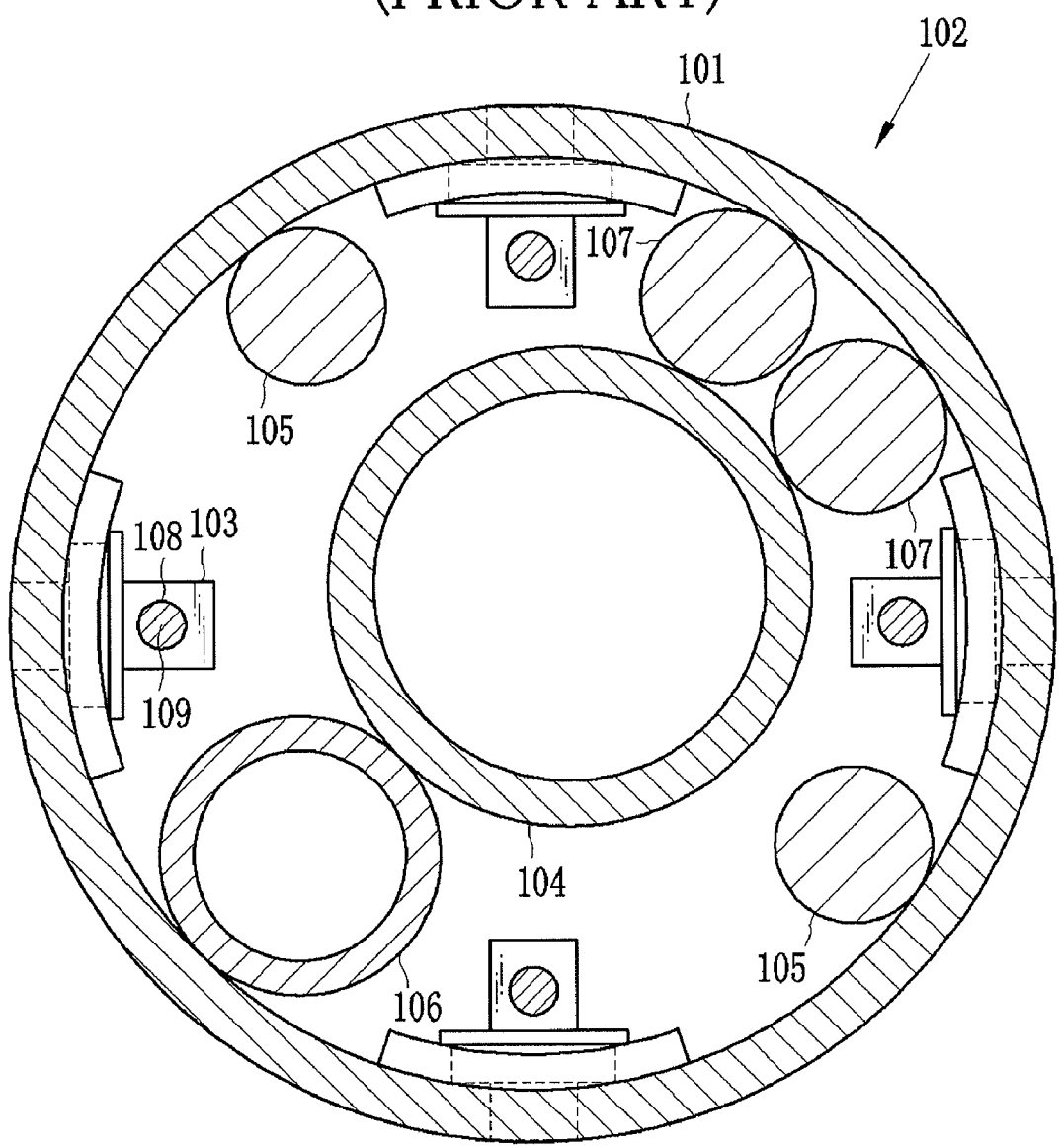
FIG. 9 is a section view of a conventional bending portion.

In addition to the operation wires 37 and 38 provided through the guide holes 36 of the coupling pins 31, as shown in FIG. 4, the forceps channel 16, the air/water channel 41, the optical fibers 50 as the light guide, the signal line 51, and the like are arranged within the joint rings 20 constituting the bending portion 18. The forceps channel 16 having the largest outer diameter among the above-mentioned internal components is disposed at the center of the joint rings 20 in the diameter direction. The air/water channel 41, the optical fibers 50 as the light guide, the signal line 51, and the like are arranged around the forceps channel 16 and contact with internal circumferential surfaces of the joint rings 20 while they are kept away from the coupling pins 31. The two branch channels 45 and 46 of the air/water channel 41 have the smaller outer diameter than the main channel 43 (see FIG. 3). The branch channels 45 and 46 are arranged side by side in the circumferential direction of the bending portion 18. A space is created inside the joint rings 20 by arranging the branch channels 45 and 46 each having the smaller outer diameter than the main channel 43. By eliminating the created space, the outer diameter of the joint ring 20 constituting the bending portion 18 is reduced compared to the outer diameter of a joint ring 101 of the conventional example (see FIG. 9). Chain double-dashed lines shown in FIG. 4 illustrate the outer diameter of the main channel 43 and that of the conventional joint ring 101 (see FIG. 9).

As described above, the air/water channel 41 is split in the flexible portion 19 at a position close to the bending portion 18, and the branch channels 45 and 46 each having the smaller diameter than the main channel 43 are arranged in the bending portion 18 as the air/water channel 41. Thus, a space is created within the joint rings 20. By eliminating the created space, the outer diameter of the bending portion 18 is reduced. Thus the diameter of the insertion section 12 is further reduced. It should be noted that in a tube to deliver fluid, such as the air/water channel 41, pressure loss increases as the inner diameter of the tube decreases and as the length of the tube increases. For this reason, the smaller-diameter branch channels 45 and 46 of the air/water channel 41, the key element for reducing the diameter of the insertion section 12, are limited to a minimum length (as short as the bending portion 18). Therefore, the pressure loss of the fluid is kept to a minimum, and thus the fluid is ejected from the nozzle without problems.

Since the diameter of the joint rings 20 is reduced, a space between the forceps channel 16 and the optical fibers 50 arranged within the joint rings 20 is reduced, which restricts the displacement of the forceps channel 16. As a result, positional fluctuation of the forceps channel 16 is prevented when the bending portion 18 is bent. This prevents the contact between the optical fibers 50 and the coupling pins 31 caused by the displacement of the forceps channel 16, and the resultant breakage of the optical fibers 50.

Second Embodiment

A forceps channel of a nasal endoscope has a smaller diameter than that of an oral endoscope so as to reduce the diameter of the insertion section. Therefore, available medical instruments are limited or only those specifically designed for the nasal endoscopes are used. For this reason, it is demanded to increase the diameter of the forceps channel without increasing the outer diameter of the insertion section. In the above first embodiment, the branch channels 45 and 46 having the small diameters are arranged within the bending portion 18 as the air/water channel 41 to create a space, and the diameter of the insertion section 12 is reduced by eliminating the created space. Alternatively, the diameter of the forceps channel may be increased by utilizing the created space.

Figure 5:
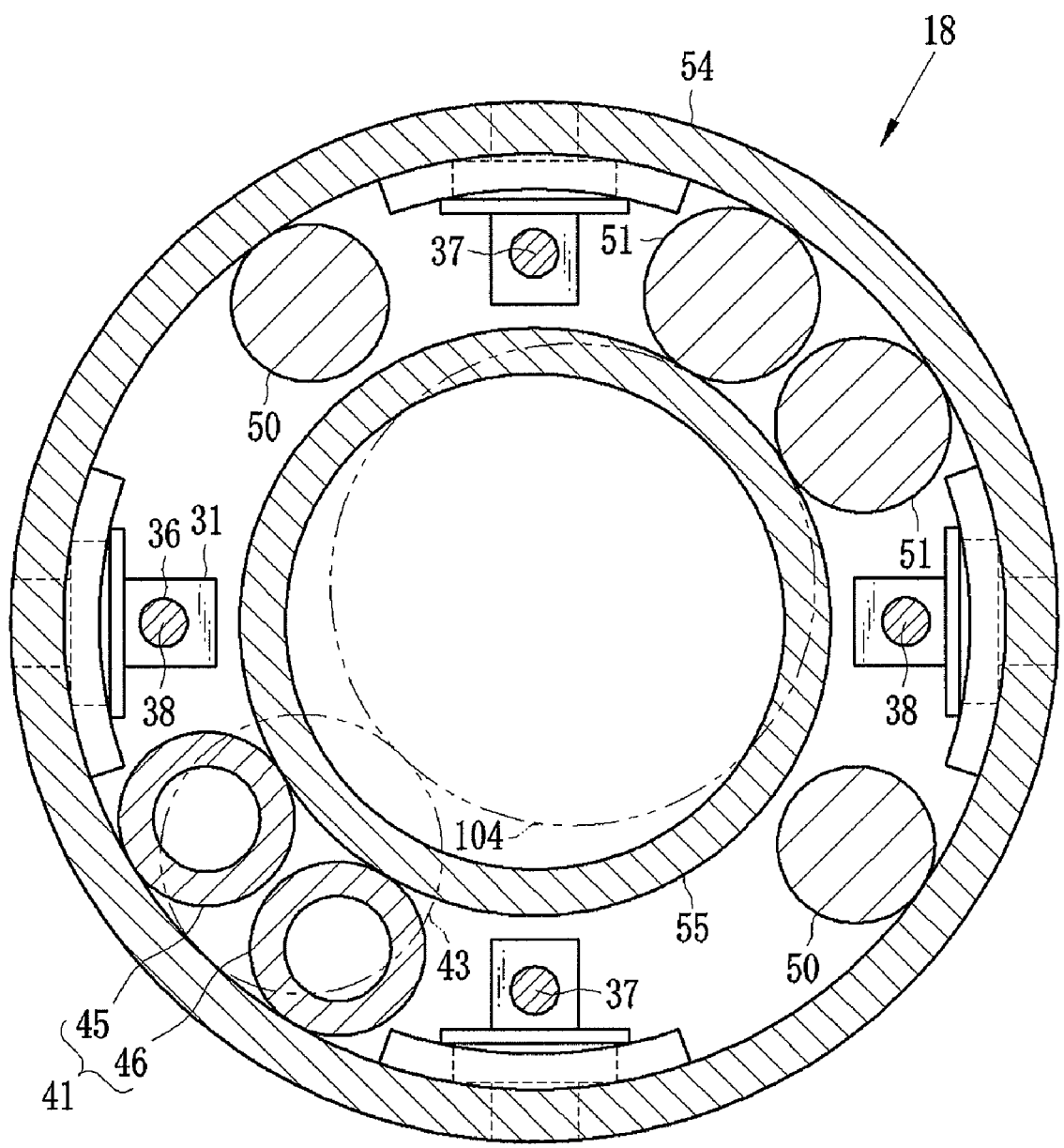
FIG. 5 is a section view of a bending portion of another embodiment.

In the second embodiment, as shown in FIG. 5, joint rings 54 are used instead of the joint rings 20 (see FIGS. 2 and 4) to constitute the bending portion 18. The joint rings 54 have the same configuration as the joint rings 20 except that the joint rings 54 have a larger outer diameter than the joint rings 20. A space is created in the bending portion 18 by using the branch channels 45 and 46 having the small diameters as the air/water channel 41. Utilizing the created space, a forceps channel 55 having a larger diameter than a conventional forceps channel 104 (see FIG. 9) is introduced. It should be noted that the joint rings 54 of this embodiment has the same outer diameter as the conventional joint rings 101 (see FIG. 9), and the outer diameter of the insertion section 12 is not larger than that of the conventional endoscope. The chain double-dashed lines shown in FIG. 5 illustrate the outer diameter of the main channel 43 and that of the conventional forceps channel 104 (see FIG. 9). An internal component similar to that within the joint rings 20 of the first embodiment is designated by the same numeral as the first embodiment, and a description thereof is omitted.

As described above, the air/water channel 41 is split in the flexible portion 19 at the position close to the bending portion 18, and the branch channels 45 and 46 with the small diameters are arranged in the bending portion 18 as the air/water channel 41. Thus, the space is created. By utilizing the created space, the diameter of the forceps channel 55 is made larger than that of the conventional forceps channel 104 (see FIG. 9).

Increase in the diameter of the forceps channel 55 reduces a space between the forceps channel 55 and the optical fibers 50. As a result, as described in the first embodiment, the breakage of the optical fibers 50 is prevented.

The diameter of the insertion section 12 is reduced in the first embodiment by eliminating the space created by arranging the branch channels 45 and 46 with the small diameters as the air/water channel 41 in the bending portion 18. On the other hand, the diameter of the forceps channel 55 is increased in the second embodiment by utilizing the created space. The created space can be eliminated or utilized as necessary. It is also possible to reduce the diameter of the insertion section 12 and increase the diameter of the forceps channel at the same time.

Third Embodiment

In the above embodiments, outer shapes of the branch channels 45 and 46 of the air/water channel 41 have circular cross-sections vertical to axis directions of the branch channels 45 and 46, respectively. However, the cross-sections may be ellipsoidal or flat-shaped. In this case, the inner shape of the branch channels 45 and 46 is circular in cross-section vertical to the axis directions thereof, respectively. In the above embodiments, the optical fibers 50 and the signal line 51 have circular cross-sections vertical to the axis directions of the optical fibers 50 and the signal line 51, respectively. Alternatively, at least one of the optical fibers 50 and the signal line 51 may have an ellipsoidal or a flat-shaped outer shape in cross-section vertical to its axis direction, at least within the bending portion 18. The optical fibers 50 and the signal line 51 are covered with tubes, respectively. The inner shapes of the tubes are circular in cross-sections vertical to the axis directions of the tubes, respectively.

Figure 6:
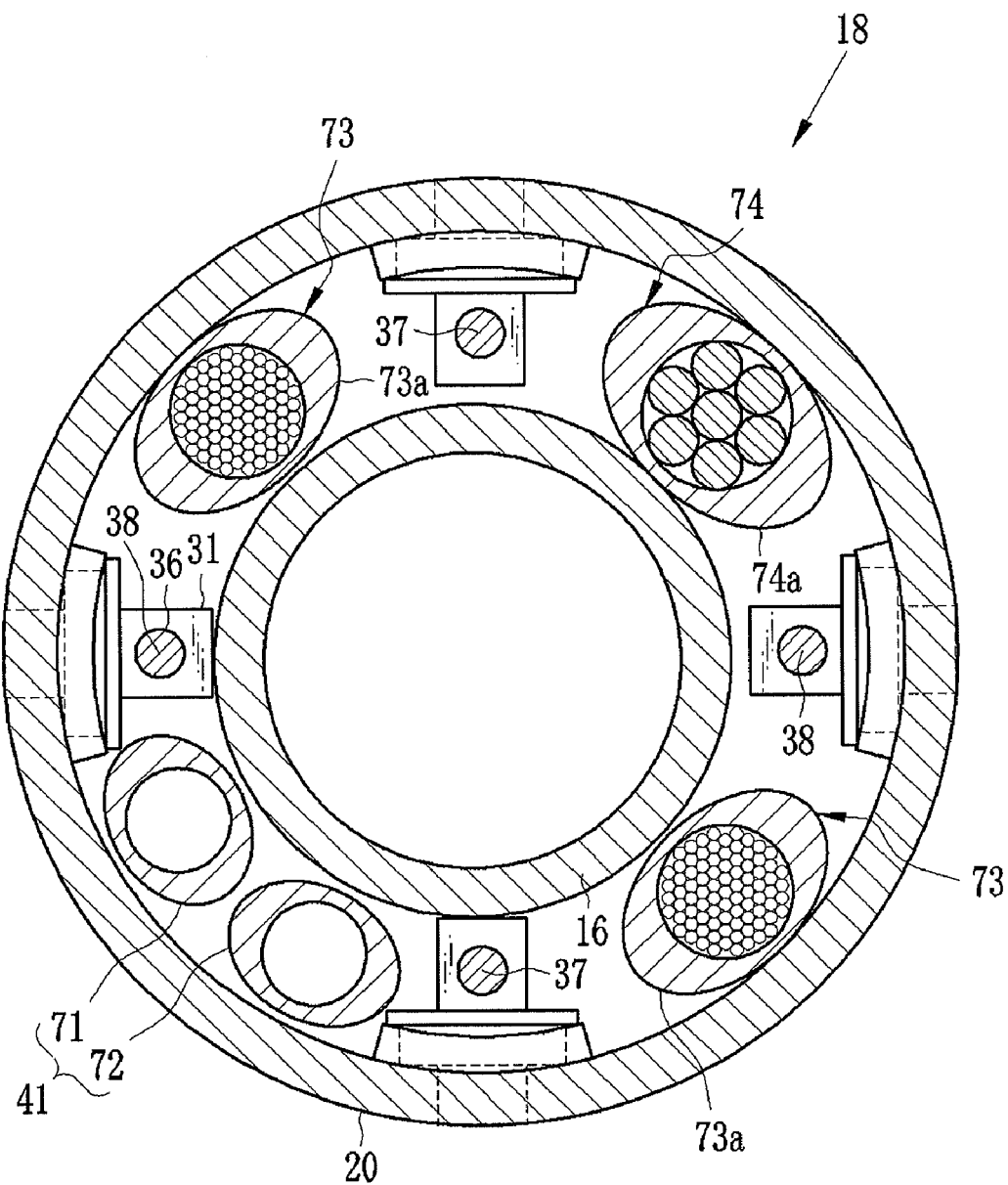
FIG. 6 is a section view of a bending portion of an embodiment in which each of an air/water channel, optical fibers as a light guide, and a signal line is ellipsoidal in cross-section.

As shown in FIG. 6, branch channels 71 and 72 of the air/water channel 41 have an ellipsoidal shape in cross-section vertical to the axis directions of the branch channels 71 and 72, and are arranged such that the major axes (the longest diameters) of the ellipsoid extend along the circumferential direction of the joint rings 20. Inner shapes of the branch channels 45 and 46 are circular in cross-sections vertical to the axis directions of the branch channels 45 and 46, respectively.

A tube 73a covers optical fibers 73 as the light guide. Within the bending portion 18, each of the optical fibers 73 (the tube 73a) has an ellipsoidal outer shape in cross-section vertical to the axis direction thereof, and is arranged such that the major axis (the longest diameter) of the ellipsoidal cross-section extends along the circumferential direction of the joint rings 20. An inner shape of the tube 73a is circular in cross-section vertical to the axis direction thereof.

A signal line 74 is covered with a tube 74a. Within the bending portion 18, the signal line 74 (the tube 74a) has an ellipsoidal outer shape in cross-section vertical to the axis direction thereof, and is arranged such that the major axis (the longest diameter) of the ellipsoid extends along the circumferential direction of the joint rings 20. An inner shape of the tube 74a is circular in cross-section vertical to the axis direction thereof. An internal component similar to that within the joint rings 20 of the first embodiment is designated by the same numeral as the first embodiment, and a description thereof is omitted.

As described above, the outer shapes of the branch channels 71 and 72 of the air/water channel 41 have ellipsoidal cross-sections vertical to the axis directions of the branch channels 71 and 72, respectively. Accordingly, bending stiffness (bending strength) of the branch channels 71 and 72 is increased compared to a case where the outer shapes of the branch channels have the circular cross-sections (see FIGS. 4 and 5). As a result, the branch channels 71 and 72 (the air/water channel 41) are prevented from damages such as buckling caused by bending operation of the bending portion 18.

Within the bending portion 18, the outer shapes of the optical fibers 73 and the signal line 74 have the ellipsoidal cross-sections vertical to the axis directions of the optical fibers 73 and the signal line 74, respectively. Accordingly, bending stiffness of the optical fibers 73 and the signal line 74 is increased compared to a case where the outer shapes of the optical fibers 73 and the signal line 74 have the circular cross-sections (see FIGS. 4 and 5). As a result, the optical fibers 73 and the signal line 74 are prevented from damages such as buckling caused by bending operation of the bending portion 18.

Fourth Embodiment

In the above embodiments, the bending portion 18 is bent in the up-and-down direction by pushing and pulling the up-and-down operation wires 37, and in the right-and-left direction by pushing and pulling the right-and-left operation wires 38. However, the configuration and the operation of the operation wires are not limited to the above.

Figure 7:
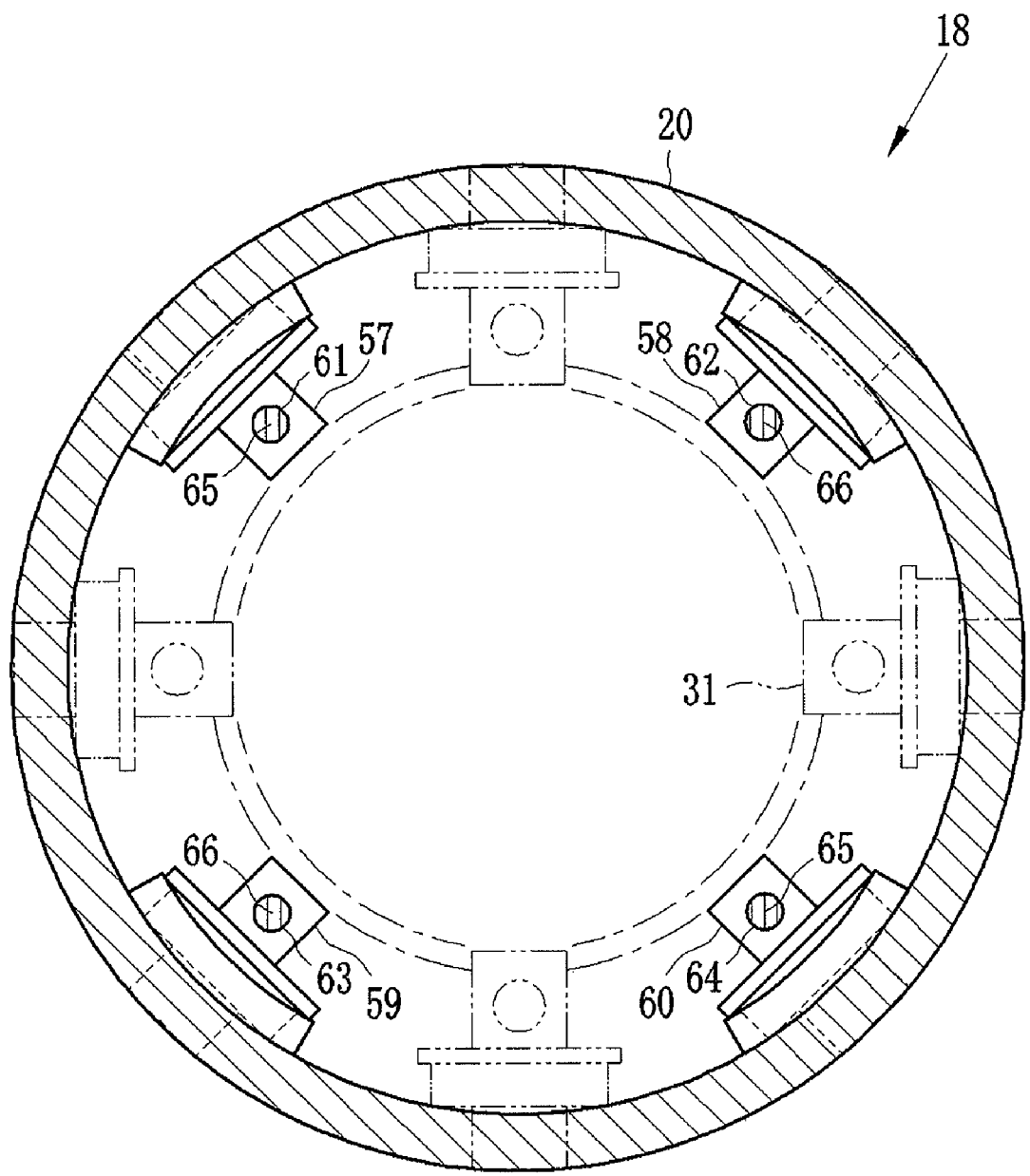
FIG. 7 is a section view of a bending portion of an embodiment in which diameters of operation wires are reduced.

In this embodiment, as shown in FIG. 7, coupling pins 57, 58, 59, and 60 are located along the internal surface of the joint rings 20 on the upper-left side, the upper-right side, the lower-left side, and the lower-right side, respectively. The coupling pins 57, 58, 59, and 60 are shifted from each other by 90° in the circumferential direction of the joint ring 20. Each of the coupling pins 57, 58, 59, and 60 deviates from each of the up-and-down and right-and-left directions of the bending directions by 45°. The coupling pins 57, 58, 59, and 60 couple the adjacent joint rings 20. Each of the coupling pins 57, 58, 59, and 60 has a small diameter section, a large diameter section, an end stop section, and a wire guide section in the same manner as the above embodiments. Guide holes 61, 62, 63, and 64 are formed to penetrate the wire guide sections of the coupling pins 57, 58, 59, and 60, respectively. A first operation wire 65 is threaded through the guide holes 61 and 64. A second operation wire 66 is threaded through the guide holes 62 and 63. One end of each of the first and the second operation wires 65 and 66 is fixed to the rigid portion 17. The other end thereof is passed through the bending portion 18, the flexible portion 19, and the operating section 13. The other end thereof is turned over in the operating section 13 through a power transmission portion (not shown) that follows the rotations of the up-and-down angle knob 22 and the right-and-left angle knob 23 (both see FIG. 1), and fixed to the rigid portion 17. The power transmission portion includes pulleys to hook the first and the second operation wires 65 and 66.

The power transmission portion pushes and pulls the first operation wire 65 or the second operation wire 66 in accordance with the operation of the up-and-down angle knob 22 or the right-and-left angle knob 23. For example, when the up-and-down angle knob 22 is rotated counterclockwise, the first operation wire 65 threaded through the guide holes 61 is pulled while the first operation wire 65 threaded through the guide holes 64 is pushed. At the same time, the second operation wire 66 threaded through the guide holes 62 is pulled while the second operation wire 66 threaded through the guide holes 63 is pushed. Thus, the bending portion 18 is bent upward. On the contrary, when the up-and-down angle knob 22 is rotated clockwise, the first operation wire 65 threaded through the guide holes 61 is pushed while the first operation wire 65 threaded through the guide holes 64 is pulled. At the same time, the second operation wire 66 threaded through the guide holes 62 is pushed while the second operation wire 66 threaded through the guide holes 63 is pulled. Thus, the bending portion 18 is bent downward.

In the same manner, when the right-and-left angle knob 23 is rotated counterclockwise, the first operation wire 65 threaded through the guide holes 61 is pulled while the first operation wire 65 threaded through the guide holes 64 is pushed. At the same time, the second operation wire 66 threaded through the guide holes 62 is pushed while the second operation wire 66 threaded through the guide holes 63 is pulled. Thereby, the bending portion 18 is bent left. On the contrary, when the right-and-left angle knob 23 is rotated clockwise, the first operation wire 65 threaded through the guide holes 61 is pushed while the first operation wire 65 threaded through the guide holes 64 is pulled. At the same time, the second operation wire 66 threaded through the guide holes 62 is pulled while the second operation wire 66 threaded through the guide holes 63 is pushed. Thereby, the bending portion 18 is bent right. The chain double-dashed lines shown in FIG. 7 illustrate the coupling pins 31 (see FIGS. 2, 4, and 5) in the above embodiments. Illustrations and descriptions of the configurations of the forceps channel, the air/water channel, and the like similar to those of the above embodiments are omitted.

Since the bending portion 18 is bent by pushing and pulling the first and the second operation wires 65 and 66, tensile load on each of the first and the second operation wires 65 and 66 is reduced by one-half compared to a case where the bending portion 18 is bent by pushing and pulling one of the up-and-down and the right-and-left operation wires 37 and 38 (see FIGS. 4 and 5). As a result, necessary tensile strengths for the first and the second operation wires are reduced, which reduce the diameters of the first and second operation wires 65 and 66. The size of the coupling pins 57, 58, 59, and 60 becomes smaller than that of the coupling pin 31 by making the diameters of the first and the second operation wires 65 and 66 smaller than the diameters of the operation wires 37 and 38. Alternate long and short dashed lines shown in FIG. 7 illustrate an inscribed circle of the coupling pins 57 to 60 and an inscribed circle of the coupling pins 31 to compare the size of the coupling pins 57 to 60 with the size of the coupling pins 31 (see, FIGS. 2, 4, and 5) in the above embodiments.

As with the above-described first and second embodiments, reducing the size of the coupling pin 31 reduces the diameter of the bending portion 18 and the insertion section 12 and/or increases the diameter of the forceps channel, and prevents break in the optical fibers as the light guide caused by the contact with the coupling pin 31.

Fifth Embodiment

In the above fourth embodiment, each of the coupling pins 57 to 60 is shifted by 90° in the circumferential direction of the joint rings 20. However, the locations of the coupling pins 57 to 60 is not limited to the above as long as the coupling pins 57 and 60 face each other, and the coupling pins 58 and 59 face each other so as not to make the bending portion 18 awkward to operate. The first operation wire 65 is threaded through the coupling pins 57 and 60. The second operation wire 66 is threaded through the coupling pins 58 and 59.

Figure 8:
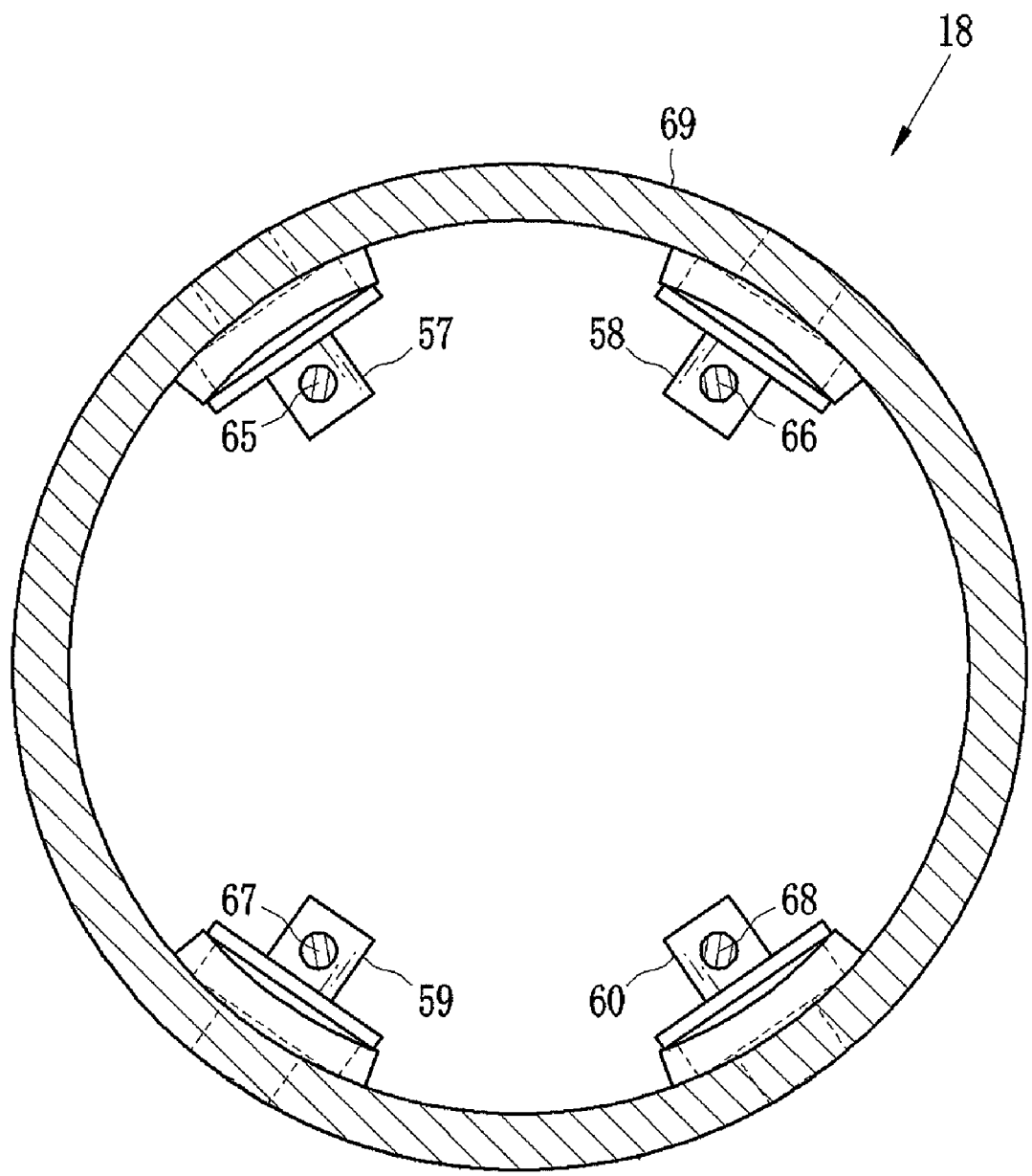
FIG. 8 is a section view of a bending portion of an embodiment in which diameters of operation wires are reduced and an arrangement of the operation wires is changed.

For example, in FIG. 8, the upper left coupling pin 57 and the upper right coupling pin 58 are located close to each other, and the lower left coupling pin 59 and the lower right coupling pin 60 are located close to each other. The coupling pins 57 and 60 face each other. The coupling pins 58 and 59 face each other. Illustrations and the descriptions of the configurations of the forceps channel, the air/water channel, and the like similar to those in the above first and the second embodiments are omitted. An internal component similar to that in the above fourth embodiment is designated by the same numeral as the fourth embodiment, and a description thereof is omitted.

As described above, spaces located apart from each other within the joint rings 20 are combined together by arranging the adjacent coupling pins 57 and 58 in proximity to each other, and the adjacent coupling pins 59 and 60 in proximity to each other. Effective utilization of the combined space increases flexibility in configuration of the internal components. The diameters of the bending portion 18 and the insertion section 12 may be reduced, and/or the diameter of the forceps channel may be increased.

In the above embodiments, the endoscope 11 may be a nasal endoscope, an oral endoscope, or other type of endoscope.

In the above embodiments, the air/water channel is split into two branch channels in the flexible portion 19 at the position close to the bending portion 18. It is also possible to split the air/water channel into more than two branch channels. It should be noted, however, the pressure loss increases as the number of the branch channels increases. Therefore, the air/water channel is split into the small number of branch channels, preferably two. In the above embodiments, the branch channels are merged. Alternatively, the branch channels may be used without being merged. In the above embodiment, one air/water channel is split into two branch channels. In a case where the air channel and the water channel are provided separately, each channel may be split into two branch channels (the total of four branch channels).

The endoscope 11 described in the above embodiments are mere examples. Any changes and modifications are possible in the present invention as long as they do not deviate from the scope of the present invention.

What is claimed is:

1. An endoscope comprising:
   a forceps channel for inserting a medical instrument into a body cavity;
   an air/water channel for feeding at least one of air and water;
   an insertion section through which said forceps channel and said air/water channel are disposed, said insertion section having a bending portion close to a distal tip of said insertion section, said air/water channel being split into plural branch channels on a proximal side from said bending portion, said branch channels passing through said bending portion;
   wherein said branch channels are merged on a distal side from said bending portion.

2. The endoscope of claim 1, wherein outer diameters of either branch channel is smaller than an outer diameter of the air/water channel, and said cross-section of said each branch channel is vertical to an axis direction of said each branch channel, and said cross-section of said air/water channel is vertical to an axis direction of said air/water channel.

3. The endoscope of claim 1, wherein said branch channels are arranged along a circumferential direction of said bending portion.

4. The endoscope of claim 1, wherein said air/water channel is split into two said branch channels.

5. The endoscope of claim 1, wherein an outer shape of said branch channel is circular in cross-section vertical to an axis direction of said branch channel.

6. The endoscope of claim 1, wherein an outer shape of said branch channel is ellipsoidal or flat-shaped in cross-section vertical to an axis direction of said branch channel.

7. The endoscope of claim 6, wherein an inner shape of said branch channel is circular in cross-section vertical to said axis direction.

8. The endoscope of claim 1, wherein a signal line for transmitting an image signal, and a light guide for guiding illumination light are disposed through said insertion section, and each of said signal line and said light guide is covered with a tube, and an outer shape of at least one of said signal line and said light guide is ellipsoidal or flat-shaped in cross-section vertical to an axis direction of said signal line or said light guide at least within said bending portion.

9. The endoscope of claim 8, wherein an inner shape of said tube covering said signal line is circular in cross-section vertical to said axis direction of said signal line, and an inner shape of said tube covering said light guide is circular in cross-section vertical to said axis direction of said light guide.

10. The endoscope of claim 1, wherein said endoscope is a nasal endoscope whose insertion section is inserted through a nostril.

11. The endoscope of claim 1, wherein the air/water channel comprises a single channel on the proximal side from said bending portion and, said single channel being split into the plural branch channels on the proximal side of the bending portion.

* * * * *